United States Patent
Ibrahim et al.

(10) Patent No.: US 7,012,072 B2
(45) Date of Patent: Mar. 14, 2006

(54) PHARMACEUTICAL OXALIPLATINUM PREPARATION FOR PARENTERAL ADMINISTRATION AND METHOD FOR OBTAINING SAME

(75) Inventors: Houssam Ibrahim, Veyner (CH); Henri Pourrat, Clermont-Ferrand (FR); Christine Deuschel, Trélex (CH)

(73) Assignee: Debiopharm S.A., Lausanne (CH)

( * ) Notice: Subject to any disclaimer, the term of this patent is extended or adjusted under 35 U.S.C. 154(b) by 85 days.

(21) Appl. No.: 10/450,260

(22) PCT Filed: Dec. 12, 2001

(86) PCT No.: PCT/CH01/00708

§ 371 (c)(1),
(2), (4) Date: Jun. 18, 2003

(87) PCT Pub. No.: WO02/47725

PCT Pub. Date: Jun. 20, 2002

(65) Prior Publication Data

US 2004/0127557 A1    Jul. 1, 2004

(30) Foreign Application Priority Data

Dec. 12, 2000   (CH) ................................ 2422/00

(51) Int. Cl.
*A61K 31/555*   (2006.01)
*A61K 31/28*    (2006.01)

(52) U.S. Cl. .................................... 514/186; 514/492
(58) Field of Classification Search ............... 514/186, 514/492
See application file for complete search history.

(56) References Cited

U.S. PATENT DOCUMENTS

| 4,439,181 A |   | 3/1984 | Blackshear et al. |
| 5,716,988 A | * | 2/1998 | Ibrahim et al. ............. 514/492 |
| 5,897,871 A |   | 4/1999 | Schlipalius |

FOREIGN PATENT DOCUMENTS

| WO | WO 96/04904 |   | 9/1998 |
| WO | WO 98/39009 |   | 9/1998 |
| WO | WO 94/12193 |   | 9/1999 |
| WO | WO 99/43355 | * | 9/1999 |
| WO | WO 00/21527 |   | 4/2000 |
| WO | WO 01/15691 |   | 3/2001 |
| WO | WO 01/15691 A1 | * | 3/2001 |

OTHER PUBLICATIONS

WPIDS Abstract No. 1999-132501 of WO 9904335 (Lundstroem et al.), 1999.*
The Merck Index, 11th edition, Budavari et al. (eds.), published 1989 by Merck & Co., Inc., p. 1401, monograph 8855.*
Remington's Pharmaceutical Sciences, 16th edition, Osol, et al. (eds), published 1980 by Mack Publishing Co. (Pa), pp. 1390 1393, 1468-1471, 1658 and 1659.*
STN Registry File Abstract No. 57-55-6 "1,2-propanediol", (2005).*

* cited by examiner

Primary Examiner—Raymond J. Henley, III
(74) Attorney, Agent, or Firm—Nixon & Vanderhye P.C.

(57) ABSTRACT

The present invention relates to a stable pharmaceutical preparation of oxaliplatin for parenteral administration, in which the oxaliplatin is in solution in a solvent at a concentration of at least 7 mg/ml, which has been subjected to an operation of wet heat treatment with steam in the saturation state and under pressure at a high temperature not exceeding 110° C. It also relates to the method for the production thereof.

8 Claims, No Drawings

PHARMACEUTICAL OXALIPLATINUM PREPARATION FOR PARENTERAL ADMINISTRATION AND METHOD FOR OBTAINING SAME

This application is the U.S. national phase of international application PCT/CH01/00708 filed 12 Dec. 2001 which designated the U.S.

The present invention relates to a pharmaceutical preparation of oxaliplatin, for parenteral administration, intended to be infused or injected. It also relates to a method for obtaining said preparation.

Oxaliplatin (INN, also called I-OHP), a complex derivative of platinum (CAS RN: 61825-94-3) described by Kidani et al. in J. Med. Chem., 1978, 21, 1315, is an antineoplastic agent used intravenously most particularly in the treatment of metastatic colorectal cancer.

Oxaliplatin, in its pure active substance form, is known to be slightly water-soluble, relatively insoluble in methanol and virtually insoluble in ethanol and acetone. More precisely, the maximum solubility of oxaliplatin at saturation in water at 37° C. is 7.9 mg/ml and is 6 mg/ml at 20° C.

Currently, it is used in the hospital environment in a lyophilized form and the liquid preparation thereof is reconstituted using a glucose solution just before it is administered, generally as an infusion of short duration.

In order to provide hospital personnel with the great advantage of, firstly, no longer having to handle a cytotoxic powder or cake during the reconstitution of the pharmaceutical preparation and, secondly, avoiding any risk of mistakenly using a reconstituting solution containing chloride ions, such as a sodium chloride solution conventionally used in this kind of operation, the serious consequence of which is to decompose the metal complex, several liquid preparations of oxaliplatin, ready to be administered parenterally by infusion, have already been proposed.

Thus, Ibrahim et al. have described, in WO 96/04904, a pharmaceutically stable preparation of oxaliplatin, ready to be administered parenterally by infusion. This preparation, which has undergone successive operations of clarifying filtration and then of aseptic filtration, consists of an aqueous solution of oxaliplatin at a concentration of approximately 2 mg/ml which contains no other adjuvants.

Mauvernay has described, in WO 00/21527, that this type of pharmaceutical preparation in which the oxaliplatin is at a concentration of approximately 2 mg/ml can advantageously be conserved and transported in a flexible infusion bag in order to simplify even further its handling during its administration to a patient. It is indicated, in that document, that the chosen material constituting this flexible bag is able to withstand the high temperatures applied during sterilization operations in an autoclave.

Anderson et al. have described, in WO 99/43355, two types of liquid formulation containing oxaliplatin. In the first, the oxaliplatin is in solution at a concentration of 2 mg/ml in pure water, as was recommended in WO 96/04904. In the second, the oxaliplatin is in solution at a concentration of 5 mg/ml in water buffered with oxalic acid. The two types of preparation, contained in sealed vials, were placed in an autoclave in order to undergo therein a wet heat finishing treatment, by subjecting them to several heat cycles at a temperature of 121° C.

These known pharmaceutical preparations satisfy most of the quality criteria set by the health authorities, in particular that of sterility.

On the other hand, their uses are greatly limited due to their very low concentrations of oxaliplatin, making it necessary to store and handle a large number of bottles or flexible bags and prohibiting the use of particularly suitable receptacles such as "prefilled" syringes or "multidose" bottles.

The present inventors have successfully managed to solve this problem engendered by the low concentrations of oxaliplatin, by making available a stable pharmaceutical preparation of oxaliplatin for parenteral administration, in which the oxaliplatin is in solution in a solvent at a concentration of at least 7 mg/ml. To do this, they found that the use of the solvent comprising a sufficient amount of at least one hydroxylated derivative chosen from 1,2-propanediol, glycerol, maltitol, sucrose and inositol made it possible to obtain preparations in which the concentration of oxaliplatin was well over 7 mg/ml.

However, they came up against some problems when it came to guaranteeing for these preparations a high degree of sterility as required by the health authorities.

Specifically, in order to guarantee better safety of pharmaceutical sterilization on an industrial scale, they preferred to use an end sterilization method involving heat sterilization, such as, for example, that described in WO 99/43355, rather than an aseptic filtration method such as, for example, that mentioned in WO 96/04904.

In doing this, they noted that the use of this method, requiring bringing the preparations to be sterilized to a temperature of 121° C. in an autoclave, did not prove to be satisfactory.

Specifically, while the degree of sterilization was quite acceptable, the appearance of cloudiness, or even of blackish particles, was noted when the autoclave was opened at the end of the process and the bottles containing the preparations were released. It was then clear that preparations of oxaliplatin exhibiting such a physical appearance would have been discarded from preparations made available to the patients.

The aim of the present invention is thus to make available a stable pharmaceutical preparation of oxaliplatin for parenteral administration, in which the oxaliplatin is in solution in a solvent at a concentration such that it allows, firstly, a clear decrease in a number of bottles or flexible bags to be stored or handled and, secondly, the use of suitable receptacles such as "prefilled" syringes or "multidose" bottles, while at the same time satisfying the criteria required by the health authorities for the approval of pharmaceutical liquid preparations, such as a high degree of sterility and a clear appearance free of solid particles.

To this effect, the present invention relates to a stable pharmaceutical preparation of oxaliplatin for parenteral administration, intended to be infused or injected, in which the oxaliplatin is in solution in a solvent at a concentration of at least 7 mg/ml, and which has been subjected to an operation of wet heat treatment with steam in the saturation state and under pressure at a high temperature not exceeding 110° C.

Preferably, said solution has been subjected to an operation of wet heat treatment at a high temperature of between 110° C. and approximately 70° C. More preferably, this high temperature is approximately 80° C.

Preferably, said operation of wet heat treatment is carried out in the course of at least two cycles composed of a phase of heating at said high temperature and then a phase of returning to and standing at ambient temperature. More preferably, the phase of heating at the high temperature lasts approximately 30 minutes and the phase of returning to and standing at ambient temperature lasts approximately 24 hours.

Preferably, the solvent of said solution containing the oxaliplatin comprises a sufficient amount of at least one hydroxylated derivative chosen from 1,2-propanediol, glycerol, maltitol, sucrose and inositol. More preferably, said solvent also comprises water.

The present invention also relates to a method for obtaining said preparation, using an operation of wet heat treatment with steam in the saturation state and under pressure in an autoclave at high temperature not exceeding 110° C.

More precisely, this method comprises, prior to said wet heat treatment operation, the implementation of the following steps:

a) bringing an amount of oxaliplatin into contact, at a temperature less than 80° C., with a sufficient amount of said solvent in order to obtain a concentration of oxaliplatin of at least 7 mg/ml; and b) establishing the mixture obtained in step a) at a temperature of between 15° C. and 30° C.

Preferably, said wet heat treatment operation comprises at least two cycles composed of a phase of heating at said high temperature, and then a phase of returning to and standing at ambient temperature. More preferably, the phase of heating at the high temperature lasts approximately 30 minutes, and the phase of returning to and standing at ambient temperature lasts approximately 24 hours.

A specialist, realizing all the advantages of this method of production, will be able to apply each of its operation to any system of aseptic filling with liquid pharmaceutical preparations which is usually found in the pharmaceutical industry, by adjusting each of the parameters mentioned to their most advantageous values, within their indicated value ranges.

Thus, the specialist will prepare a filling solution in which the oxaliplatin is at a concentration of at least 7 mg/ml in the appropriate solvent. He or she will then fill the appropriate sterilized receptacles, on a continuous or batch filling system, preferably under an atmosphere of an inert gas. These receptacles will, depending on the case, be closed with a stopper or sealed, and then placed in an autoclave in order to undergo therein the operations of wet heat treatment with steam in the saturation state and under pressure in an autoclave at a high temperature not exceeding 110° C.

The invention, and its advantages, will be described hereinafter using the following examples:

EXAMPLE 1

Preparation of Solutions Containing Oxaliplatin at a Concentration of 10 mg/ml

In the laboratory, an oxaliplatin powder (250 mg) is placed in a 50 ml receptacle graduated at 25 ml. One of the co-solvents chosen from 1,2-propanediol, glycerol and maltitol, respectively, is introduced into the receptacle at the same time as or prior to the addition of water to make the volume up to 25 ml, according to the corresponding volume/volume or weight/volume ratios as indicated in the various tables.

Two other co-solvents, namely sucrose and inositol, were also used and results identical to those described in the examples were obtained.

The mixtures obtained are, where appropriate, brought to a temperature not exceeding 80° C. and to atmospheric pressure in order to finish the complete dissolution of the oxaliplatin.

After returning to ambient temperature, namely approximately 20° C., a clarifying filtration operation is optionally carried out in order to ensure clarity.

EXAMPLE 2

Comparative Test for Treatment at a Temperature of Approximately 121° C.

The mixtures as obtained by applying the method described in example 1, and according to the relative amounts indicated in table 1, were subjected to an operation of wet heat treatment at a temperature of 121° C. in an autoclave according to the methods well known to a specialist.

The results observed at the end of the treatment, after returning to ambient temperature, are described in table 1.

TABLE 1

| | Active substance | | |
|---|---|---|---|
| | Oxaliplatin | Oxaliplatin | Oxaliplatin |
| Concentration | 10 mg/ml | 10 mg/ml | 10 mg/ml |
| Solvent | 1,2-propanediol/ water 50/50 (V/V) | 85% glycerol/ water 50/50 (V/V) | maltitol/ water 50% (m/V) |
| Heating temperature and time | 121° C. ± 2 30 min | 121° C. ± 2 30 min | 121° C. ± 2 30 min |
| Observations | presence of black precipitate | presence of black precipitate | presence of black precipitate |

At a temperature of 121° C., the appearance of a water-insoluble black precipitate is observed.

EXAMPLE 3

Comparative Test for Treatment at Temperatures of Approximately 120° C. and of Approximately 110° C.

Various solutions of oxaliplatin at a concentration of 10 mg/ml, obtained as previously, and degassed beforehand with argon, were subjected to operations of wet heat treatment at temperatures of 120° C. and 110° C., respectively.

The results observed at the end of the treatment, after returning to ambient temperature, are described in tables 2 and 3.

TABLE 2

| | Active substance | | |
|---|---|---|---|
| | Oxaliplatin | Oxaliplatin | Oxaliplatin |
| Concentration | 10 mg/ml | 10 mg/ml | 10 mg/ml |
| Solvent | 1,2-propanediol/ water | 85% glycerol/ water | maltitol/ water |
| degassed with argon | 20/20 (V/V) | 20/20 (V/V) | 50% (m/V) |
| Heating temperature and time | 120° C. ± 2 150 min | 120° C. ± 2 150 min | 120° C. ± 2 150 min |
| Observation after storage | presence of black precipitate | presence of black precipitate | presence of black precipitate |

TABLE 3

| | Active substance | | |
|---|---|---|---|
| | Oxaliplatin | Oxaliplatin | Oxaliplatin |
| Concentration | 10 mg/ml | 10 mg/ml | 10 mg/ml |
| Solvent degassed with argon | 1,2-propanediol/ water 20/20 (V/V) | 85% glycerol/ water 20/20 (V/V) | maltitol/ water 50% (m/V) |
| Heating temperature and time | 110° C. ± 2 120 min | 110° C. ± 2 120 min | 110° C. ± 2 120 min |
| Observation after storage | presence of black precipitate | presence of black precipitate | presence of black precipitate |

At the respective temperatures of 120° C. and 110° C., the appearance of a water-insoluble black precipitate is observed.

EXAMPLE 4

Comparative Test for Treatment of a Solution in a Supersaturated State, at a Temperature of 120° C.

A supersaturated aqueous solution of oxaliplatin, containing 10 mg of oxaliplatin per 10 mg of water, was prepared without adding a co-solvent, by subjecting it to a temperature of approximately 80° C. at atmospheric pressure for a few minutes.

After returning to ambient temperature, this preparation was subjected to an operation of wet heating at a temperature of 120° C.

The results are described in table 4.

TABLE 4

| Active substance | Oxaliplatin |
|---|---|
| Concentration | 10 mg/ml |
| Solvent | water for injectable preparation |

TABLE 4-continued

| Active substance | Oxaliplatin |
|---|---|
| Heating temperature and time | 120° C. ± 2 90 min |
| Observation after storage | presence of black precipitate |

At the temperature of 120° C., the appearance of a water-insoluble black precipitate is observed.

EXAMPLE 5

Test for Treatment at Temperatures of Approximately 80° C. and 70° C.

Solutions of oxaliplatin at concentrations of, respectively, 10 mg/ml and 12 mg/ml, containing one of the following hydroxylated derivatives: 1,2-propanediol, glycerol and maltitol, were subjected to an operation of wet heat treatment at respective temperatures of 70° C. and 80° C.

The results observed 24 hours after the end of the treatment, and a return to ambient temperature, are described in table 5.

TABLE 5

| | Active substance | | | |
|---|---|---|---|---|
| | Oxaliplatin | Oxaliplatin | Oxaliplatin | Oxaliplatin |
| Concentration | 10 mg/ml | 10 mg/ml | 10 mg/ml | 12 mg/ml |
| Solvent | 1,2-propanediol/ water 50/50 (V/V) | 85% glycerol/ water 50/50 (V/V) | maltitol/ water 50% (m/V) | maltitol/ water 30% (m/V) |
| Heating temperature and time | 70° C. ± 2 30 min | 70° C. ± 2 30 min | 70° C. ± 2 30 min | 80° C. ± 2 30 min |
| Observatios | complete solubilization of the substance. No presence of precipitate. Solution has clear appearance | complete solubilization of the substance. No presence of precipitate. Solution has clear appearance | complete solubilization of the substance. No presence of precipitate. Solution has clear appearance | complete solubilization of the substance. No presence of precipitate. Solution has clear appearance |

At respective temperatures of 70° C. and 80° C., the appearance of a water-insoluble black precipitate is not observed.

EXAMPLE 6

Test for Treatment of a Solution in the Supersaturated State, at Temperatures of Approximately 80° C.

An aqueous solution of oxaliplatin as prepared in example 4 was subjected to an operation of wet heating at a temperature of 80° C. The results are described in table 6.

TABLE 6

| Active substance | Oxaliplatin |
|---|---|
| Concentration | 10 mg/ml |
| Solvent | water for injectable preparation |
| Heating temperature and time | 80° C. ± 2 30 min |

TABLE 6-continued

| Active substance | Oxaliplatin |
|---|---|
| Observation after storage | no presence of precipitate solution has a clear appearance |

At the temperature of 80° C., no precipitate was observed.

EXAMPLE 7

Operation Involving Sterilization of Solutions of Oxaliplatin at a Concentration of 10 mg/ml by Wet Heat Treatment at a Temperature of 80° C.

Various solutions of oxaliplatin at a concentration of 10 mg/ml, obtained using the method described in example 1 and by applying the relative amounts of various constituents as indicated in table 7, were prepared.

They were then subjected to operations of wet heat sterilization by carrying out three successive cycles of heating at a temperature of 80° C., followed by a return to an ambient temperature of approximately 20° C. The respective durations of the various phases of these cycles are indicated in table 7.

The solutions thus treated were kept, before observation, at refrigerator temperature for 72 hours. The results are described in table 7.

TABLE 7

| | Active substance | | |
|---|---|---|---|
| | Oxaliplatin | Oxaliplatin | Oxaliplatin |
| Concentration | 10 mg/ml | 10 mg/ml | 10 mg/ml |
| Solvent | 1,2-propanediol/ water for injectable preparation 50/50 (V/V) | 85% glycerol/ water for injectable preparation 50/50 (V/V) | maltitol/ water for injectable preparation 50% (m/V) |
| Heating temperature and time | 80° C. ± 2 30 min | 80° C. ± 2 30 min | 80° C. ± 2 30 min |
| Time standing at approx. 20° C. | 24 h | 24 h | 24 h |
| Heating temperature and time | 80° C. ± 2 30 min | 80° C. ± 2 30 min | 80° C. ± 2 30 min |
| Time standing at approx. 20° C. | 24 h | 24 h | 24 h |
| Heating temperature and time | 80° C. ± 2 30 min | 80° C. ± 2 30 min | 80° C. ± 2 30 min |
| Observations | complete solubilization of the substance. No presence of precipitate. Solution has a clear appearance | complete solubilization of the substance. No presence of precipitate. Solution has a clear appearance | complete solubilization of the substance. No presence of precipitate. Solution has a clear appearance |

At the end of each of the sterilizing treatments, a sterilization test was carried out on each one of the preparations, according to the protocol recommended in chapter 2.6.1. STERILITY of the European Pharmacopoeia, 3rd edition, applying the membrane filtration method.

It was found that all the results were satisfactory. No contaminating trace of microorganisms was found.

From the preceding results, it results that pharmaceutical preparations of oxaliplatin for parenteral administration, at a concentration of greater than or equal to 7 mg/ml, can be obtained, while being sterile and free of insoluble black precipitate, through sterilization by carrying out successive heating operations at temperatures of 80° C.

The invention claimed is:

1. A stable pharmaceutical preparation of oxaliplatin for parenteral administration, in which the oxaliplatin is in solution in a solvent at a concentration of at least 7 mg/ml, and wherein the solution of oxaliplatin has been subjected to an operation of wet heat treatment with steam in the saturation state and under pressure at a temperature not exceeding 110° C., and wherein the solvent of said solution which contains the oxaliplatin comprises a sufficient amount of at least one hydroxylated derivative chosen from 1,2-propanediol, glycerol, maltitol, sucrose and inositol.

2. The stable pharmaceutical preparation of oxaliplatin as claimed in claim 1, characterized in that said solution has been subjected to an operation of wet heat treatment at a temperature of between 110° C. and about 70° C.

3. The stable pharmaceutical preparation of oxaliplatin as claimed in claim 1, characterized in that said solution has been subjected to an operation of wet heat treatment at a temperature of about 80° C.

4. The stable pharmaceutical preparation of oxaliplatin as claimed in claim 1, characterized in that said wet heat treatment operation is carried out in the course of at least two cycles composed of a phase of heating at said temperature and then a phase of returning to aid standing at ambient temperature.

5. The stable pharmaceutical preparation of oxaliplatin as claimed in claim 4, characterized in that said phase of heating at the temperature lasts about 30 minutes and the phase of returning to and standing at ambient temperature lasts about 24 hours.

6. The stable pharmaceutical preparation of oxaliplatin as claimed in claim 1, characterized in that said solvent also comprises water.

7. A method for obtaining a stable pharmaceutical preparation of oxaliplatin for parenteral administration, in which the oxaliplatin is in solution in a solvent at a concentration of at least 7 mg/ml, comprising dissolving oxaliplatin in a solvent comprising a sufficient amount of at least one hydroxylated derivative chosen from 1,2-propanediol, glycerol, maltitol, sucrose and inositol, and subjecting the solution to an operation of wet heat treatment with steam in the saturation state and under pressure at a temperature not exceeding 110° C.

8. The method as claimed in claim 7, which also comprises, prior to said wet heat treatment operation, the implementation of the following steps:
   a) bringing an amount of oxaliplatin into contact, at a temperature less than 80° C., with a sufficient amount of said solvent in order to obtain a concentration of oxaliplatin of at least 7 mg/ml; and
   b) establishing the mixture obtained in step a) at a temperature of between 15° C. and 30° C.

* * * * *